(12) United States Patent
Kirchner et al.

(10) Patent No.: US 9,247,885 B2
(45) Date of Patent: Feb. 2, 2016

(54) HEART MONITOR

(75) Inventors: Jens Kirchner, Erlangen (DE); Michael Lippert, Ansbach (DE)

(73) Assignee: BIOTRONIK SE & Co. KG (DE)

( * ) Notice: Subject to any disclaimer, the term of this patent is extended or adjusted under 35 U.S.C. 154(b) by 0 days.

(21) Appl. No.: 13/185,881

(22) Filed: Jul. 19, 2011

(65) Prior Publication Data

US 2012/0035436 A1    Feb. 9, 2012

Related U.S. Application Data

(60) Provisional application No. 61/371,175, filed on Aug. 6, 2010.

(51) Int. Cl.
*A61N 1/365* (2006.01)
*A61B 5/04* (2006.01)
*A61B 5/0215* (2006.01)
*A61N 1/368* (2006.01)
*A61B 5/022* (2006.01)
*A61B 5/02* (2006.01)
*A61N 1/372* (2006.01)
*A61N 1/39* (2006.01)

(52) U.S. Cl.
CPC ............ *A61B 5/0215* (2013.01); *A61B 5/04* (2013.01); *A61N 1/36521* (2013.01); *A61N 1/36564* (2013.01); *A61N 1/36571* (2013.01); *A61N 1/36585* (2013.01); *A61B 5/02028* (2013.01); *A61N 1/3684* (2013.01); *A61N 1/37211* (2013.01); *A61N 1/3962* (2013.01)

(58) Field of Classification Search
CPC .. A61B 5/02028; A61B 5/04; A61N 1/36521; A61N 1/36564; A61N 1/36571; A61N 1/36585; A61N 1/3684
USPC ............... 600/508; 607/17–18, 23–24, 20, 42
See application file for complete search history.

(56) References Cited

U.S. PATENT DOCUMENTS

| | | | |
|---|---|---|---|
| 4,674,518 A | | 6/1987 | Salo |
| 4,846,195 A | * | 7/1989 | Alt ................................ 600/595 |
| 5,154,171 A | * | 10/1992 | Chirife ............................ 607/24 |
| 5,417,717 A | | 5/1995 | Salo et al. |
| 6,405,085 B1 | | 6/2002 | Graupner et al. |
| 6,494,832 B1 | | 12/2002 | Feldman et al. |
| 7,130,689 B1 | * | 10/2006 | Turcott ............................ 607/27 |
| 7,395,114 B2 | | 7/2008 | Czygan et al. |
| 7,519,422 B2 | | 4/2009 | Lippert et al. |
| 7,570,990 B2 | | 8/2009 | Faber et al. |
| 7,593,766 B2 | | 9/2009 | Faber et al. |
| 7,630,770 B2 | * | 12/2009 | Limousin et al. ............... 607/42 |
| 7,702,389 B2 | | 4/2010 | Czygan et al. |
| 7,725,181 B1 | * | 5/2010 | Bornzin et al. .................... 607/9 |
| 7,761,141 B2 | * | 7/2010 | Hirsh ............................. 600/513 |

(Continued)

*Primary Examiner* — William Levicky
(74) *Attorney, Agent, or Firm* — Craig A. Fieschko, Esq.; DeWitt Ross & Stevens S.C.

(57) ABSTRACT

A medical device includes a preload determination unit for determining the preload of a ventricle for a cardiac cycle and providing a preload value representing the preload; a contractility determination unit for determining the contractility of the ventricle for the cardiac cycle and providing a contractility value representing the contractility; and an evaluation unit connected to the preload determination unit and the contractility determination unit, with the evaluation unit being configured to evaluate contractility values versus associated preload values.

17 Claims, 6 Drawing Sheets

(56) References Cited

U.S. PATENT DOCUMENTS

| | | |
|---|---|---|
| 7,844,335 B2 | 11/2010 | Lippert et al. |
| 7,883,469 B2 | 2/2011 | Lippert et al. |
| 2002/0016548 A1* | 2/2002 | Stadler et al. .................. 600/509 |
| 2003/0074029 A1 | 4/2003 | Deno et al. |
| 2004/0172079 A1 | 9/2004 | Chinchoy |
| 2005/0027323 A1 | 2/2005 | Mulligan et al. |
| 2005/0049646 A1 | 3/2005 | Czygan et al. |
| 2007/0043299 A1* | 2/2007 | Wariar et al. ................. 600/514 |
| 2007/0073171 A1* | 3/2007 | Cho et al. ...................... 600/486 |
| 2007/0156059 A1* | 7/2007 | Vitali et al. .................... 600/529 |
| 2007/0191724 A1* | 8/2007 | Hirsh ............................. 600/523 |
| 2008/0091114 A1* | 4/2008 | Min et al. ...................... 600/508 |
| 2008/0097226 A1 | 4/2008 | McConnell |
| 2008/0195167 A1* | 8/2008 | Ryan .............................. 607/23 |
| 2008/0300504 A1 | 12/2008 | Lefkov et al. |
| 2009/0216145 A1 | 8/2009 | Skerl et al. |
| 2010/0113944 A1* | 5/2010 | Min et al. ...................... 600/486 |
| 2010/0113945 A1* | 5/2010 | Ryan .............................. 600/486 |
| 2010/0114230 A1* | 5/2010 | Audit et al. .................... 607/18 |

\* cited by examiner

HEART MONITOR

CROSS-REFERENCE TO RELATED APPLICATIONS

This application claims priority under 35 U.S.C. §119(e) to U.S. Provisional Patent Application 61/371,175 filed Aug. 6, 2010, the entirety of which is incorporated by reference herein.

FIELD OF THE INVENTION

The invention relates to a heart monitor for the automatic recognition of states of possible cardiac insufficiency.

BACKGROUND OF THE INVENTION

There are a number of known indicators of cardiac output, with an example being the contractility of the right ventricle. The contractility describes the force and the speed of a myocardial contraction. The contractility is controlled by three mechanisms: direct control by the autonomous nervous system (ANS); the so-called Frank-Starling mechanism; and the so-called Bowditch effect (force-frequency coupling). The main mechanism, control of the circulatory regulation by the autonomous nervous system, increases the contractility and the heart rate when elevated metabolic demand exists, for example, in the event of physical or mental exertion, in order to ensure a suitable blood supply.

In patients having chronic heart failure (HF), the myocardial contractility decreases to a low level and the interventricular synchronization is worsened. This is accompanied by a low ejection fraction (EF), and by a lesser quality of life and a high mortality. HF occurs frequently in the population. HF patients are treated using various medications which influence the inotropic state in order to stabilize the heart rate, such as beta blockers, but positive inotropic medications, such as glycosides, are also used in order to elevate the contractility. More recently, HF patients have been treated using resynchronization therapy devices, such as three-chamber cardiac pacemakers or defibrillators. The goal of such cardiac resynchronization therapy (CRT) is to synchronize the two ventricles of a heart through biventricular stimulation, in order to improve the time behavior of the ventricles and thus the cardiac output.

The contractility is therefore an important variable to observe, in particular for HF patients. Such observation is important in order to observe the status of the patient and the alleviation or progress of their illness; to establish and observe the resynchronization therapy of the heart (cardiac resynchronization therapy, CRT); and/or to observe the status of treatment via medication. Information about the contractility can additionally be used for the purpose of optimizing cardiac pacemaker therapy or a therapy by an implantable cardioverter/defibrillator (ICD).

Although the contractility is a variable of great importance, it is difficult to measure in clinical practice. Determining the contractility on the basis of a maximum ventricular pressure gradient $(dP/dt)_{max}$ in the right or left ventricle is known. A left-ventricular ejection fraction (EF) can additionally be determined using echocardiography. Examination of the right ventricle using echocardiography is difficult for anatomical reasons, although information about the right ventricle is very important for a complete examination. Both procedures—the pressure measurement and the echocardiography—are time-consuming and costly. The ventricular pressure measurement requires an invasive procedure which situates a pressure catheter in one or both ventricles, and can only be performed during an electrophysiological study or during the implantation of a cardiac pacemaker or cardioverter/defibrillator Implants which allow the contractility of a heart to be ascertained are described, for example, in U.S. Pat. Nos. 4,674,518; 5,417,717; and 7,519,422. A measurement of the change of the ventricle volume is performed therein using the pressure gradient dP/dt and using impedance plethysmography.

SUMMARY OF THE INVENTION

The invention provides an improved device for recognizing cardiac insufficiency, and involves a medical device which includes:
- a preload determination device which determines the preload of a ventricle for a respective cardiac cycle and calculates a preload value representing a respective preload;
- a contractility determination device which determines the contractility of the ventricle and calculates a contractility value representing a respective preload, and
- an evaluation unit connected to the preload determination device and the contractility determination device, wherein the evaluation unit is configured to analyze a series of contractility values in consideration of respective associated preload values.

The medical device thus evaluates the respective contractility values, which are acquired by the contractility determination device of the respective ventricle, as a function of the preload values, which are acquired by the preload determination device of the respective ventricle, and considers the assignment of the preload values to the contractility values.

The invention uses the finding that prior methods, which determine an averaged $(dP/dt)_{max}$, neglect the differences in the underlying preloads. The functional dependence of contractility and preload is thus not determined by prior methods and devices.

The invention can derive a measure for the Frank-Starling mechanism from the respiratory variations of $(dP/dt)_{max}$. This measure is used for recognizing and monitoring right or left cardiac insufficiency. Thus, the invention allows a recognition of cardiac insufficiency by quantification of the Frank-Starling effect.

The invention may also use the finding that $(dP/dt)_{max}$ forms a measure of the contractility of the respective examined ventricle, and that the pressure variations in the thorax and abdomen caused by respiration cause the preload to vary spontaneously. The strength of this preload variation may be determined from respiratory pressure variations (for example, of maximum or end-diastolic pressure).

Thus, the Frank-Starling mechanism can be studied solely from a blood pressure measurement, i.e., the dependence of the contractility on the preload can be reconstructed. This is diagnostically relevant in that the contractility of the right/left ventricle is directly related to the development of right/left heart failure.

The pressure gradient between thorax and abdomen varies periodically owing to respiration, which results in periodic variations of the blood stream in the right ventricle. This change of the preload results in a change of the contractility (Frank-Starling effect) in the healthy heart, which is read off at $(dP/dt)_{max}$ of the right-ventricular or pulmonary-arterial pressure. A comparable effect also occurs in the left ventricle. Respiration thus results in an oscillation of $(dP/dt)_{max}$ in both ventricles and in the arteries close to the heart.

The effect in the right ventricle (RV) and in the pulmonary artery (PA) leading therefrom is as follows. During inhalation, a partial vacuum is generated in the thorax, which expands the thoracic vessels. As a result, the vascular resistance is reduced, and additionally a suction effect is exerted on the blood in the adjoining vessels. The pressure in the abdomen is simultaneously elevated by the lowering of the diaphragm, which results in a vascular constriction in the abdomen, and thus in a pumping effect of the blood into the adjoining vessels.

An amplified venous inflow of blood from the abdomen into the thorax therefore occurs during inhalation. The result is a strengthened filling of the right ventricle, which results in an increase of the contractility (Frank-Starling effect). This is indicated by an increase of $(dP/dt)_{max}$, which is measured in the right ventricle or in the associated pulmonary artery.

The reverse effect is observed during exhalation. An oscillation of $(dP/dt)_{max}$ therefore results, which reaches its maximum at or shortly after the maximum inhalation.

The effect in the left ventricle (LV) and in the aorta (Ao) is as follows. During inhalation, the lungs are stretched, so that the capacity of the pulmonary vessels increases. The venous backflow to the left ventricle thus decreases. The contractility and thus $(dP/dt)_{max}$ decrease corresponding to the reduced preload. An oscillation of $(dP/dt)_{max}$ therefore results, which reaches its minimum at or shortly after the maximum inhalation. The effect in the LV or the aorta is thus phase-shifted by 180° with respect to the effect in the RV or the pulmonary artery.

Following are several preferred versions of the heart monitor according to the invention:

The contractility determination device of the respective ventricle preferably includes a pressure sensor configured to acquire a blood pressure. Positioning of the sensor in the heart or in an artery close to the heart is expedient.

The preload determination device preferably also includes a pressure sensor for acquiring a blood pressure, which can be the same sensor as that used for determining the contractility by the contractility determination device.

The pressure sensor can be implemented as an implantable sensor, and can be integrated in an electrode line provided as a portion of an implantable cardiac stimulator, for example.

Instead of (or in addition to) a pressure sensor for acquiring the respiratory curve of characteristic points of the blood pressure, a device which acquires the intrathoracic impedance and/or the stroke volume may also be provided. These may also be both a component of the preload determination device and also a component of the contractility determination device.

Devices for acquiring the intrathoracic impedance and/or the stroke volume are known, for example, from U.S. Pat. No. 7,395,114, the contents of which are hereby incorporated by reference. Impedance measurement is also known from US Patent Appl'n. Publ'n. 2008/0300504 and US Patent Appl'n. Publ'n. 2009/0216145, the contents of which are also incorporated herein with respect to the impedance measurement.

Preferably, the medical device has a sensor for determining the activity or the position (e.g., upright or recumbent) of the patient, i.e., an activity and/or position sensor. This sensor is at least indirectly connected to the evaluation unit. For example, a blood oxygen sensor, which acquires the oxygen saturation of the blood, or a movement sensor is suitable as the activity sensor. Accelerometers or other tilt/level sensors can be used as the position sensor.

The preload determination device are preferably configured to determine and evaluate pressure values which represent the thoracic pressure, in particular at characteristic times of the cardiac cycle, such as the end-diastolic pressure or the maximum pressure. Additionally or alternatively, the preload determination device can determine and evaluate a thoracic pressure differential, i.e., the difference of the thoracic pressure and the minimum of the respiratory cycle.

In a preferred version of the invention, the preload determination device is configured to consider a starting value of the activity or position sensor when determining the preload.

The contractility determination device is preferably configured to derive a measure for the contractility of the observed ventricle from pressure values, in particular pressure values representing the ventricular pressure. In a preferred version of the invention, the contractility determination device is configured to derive a measure for the contractility of the observed ventricle from the maximum of the derivative of the pressure according to time, i.e., from $(dP/dt)_{max}$.

The evaluation unit is preferably configured to determine a functional relationship between the contractility values and the preload values. For this purpose, the evaluation unit is preferably configured to prepare and evaluate a preload-contractility graph. In particular, the evaluation unit can be configured to derive values of one or more of minimum values, maximum values, and maximum slope from the preload-contractility graph. In addition, the variation of parameters which are determined from the preload-contractility graph may be observed over time and trend parameters may be determined.

A heart monitor exemplifying the invention thus includes a sensor system for:

A. measuring a variable from which a measure for the preload of a ventricle may be determined by cardiac cycle, preferably a measure of the blood pressure (venous vessels would also be suitable for this purpose);

B. measuring a variable from which a measure for the contractility of the ventricle may be determined by heart cycle, preferably a measure of the blood pressure in a ventricle or an artery close to the heart; and C. optionally measuring further variables, such as the activity of the patient (via oxygen saturation sensors, movement sensors, etc.) or the position of the patient.

The measured variables which are determined according to A and B above may be identical.

The data analysis is performed in one or more suitable components in an implant, an external device, or a computing center.

The data evaluation by the evaluation unit preferably includes the following steps:

1. Determining a measure for the preload of the observed ventricle from the measured variable determined according to A, such as thoracic pressure, determined in particular from characteristic points of the cardiac cycle, for example, from end-diastolic or maximum pressure; and/or thoracic pressure differential, i.e., difference of the thoracic pressure to the minimum of the respiratory cycle.

Additional sensor variables may also be incorporated, such as position of the patient, and/or activity of the patient, determined from movement/acceleration sensors, oxygen saturation, etc., for example.

2. Determining a measure for the contractility of the observed ventricle from the measured variable determined according to B, in particular $(dP/dt)_{max}$.

3. Determining the functional relationship between the two measures determined in steps 1 and 2, e.g., by plotting in a preload-contractility graph.

4. Deriving one or more parameters from the graph determined in step 3, such as minimum and maximum value, slopes, etc.

Using the described system, the Frank-Starling effect can be quantified, i.e., the contractility of one of the ventricles can be determined as a function of preload, thereby allowing the cardiac insufficiency of the ventricle to be recognized and monitored.

The above-described method is preferably implemented in parallel in the systemic circulation and in the pulmonary circulation, with the heart monitor being appropriately configured and having two pressure sensors, for example, one of which is implemented to be positioned in the right ventricle or in the pulmonary artery and the other of which is implemented to be positioned in the left ventricle or in the aorta or in a peripheral artery, for example. The variables obtained therefrom are compared, from which further diagnostically relevant parameters may be derived

BRIEF DESCRIPTION OF THE DRAWINGS

The invention will be explained in greater detail on the basis of exemplary versions with reference to the FIG.s. In the FIG.s.

DETAILED DESCRIPTION OF EXEMPLARY VERSIONS OF THE INVENTION

Figure 1:
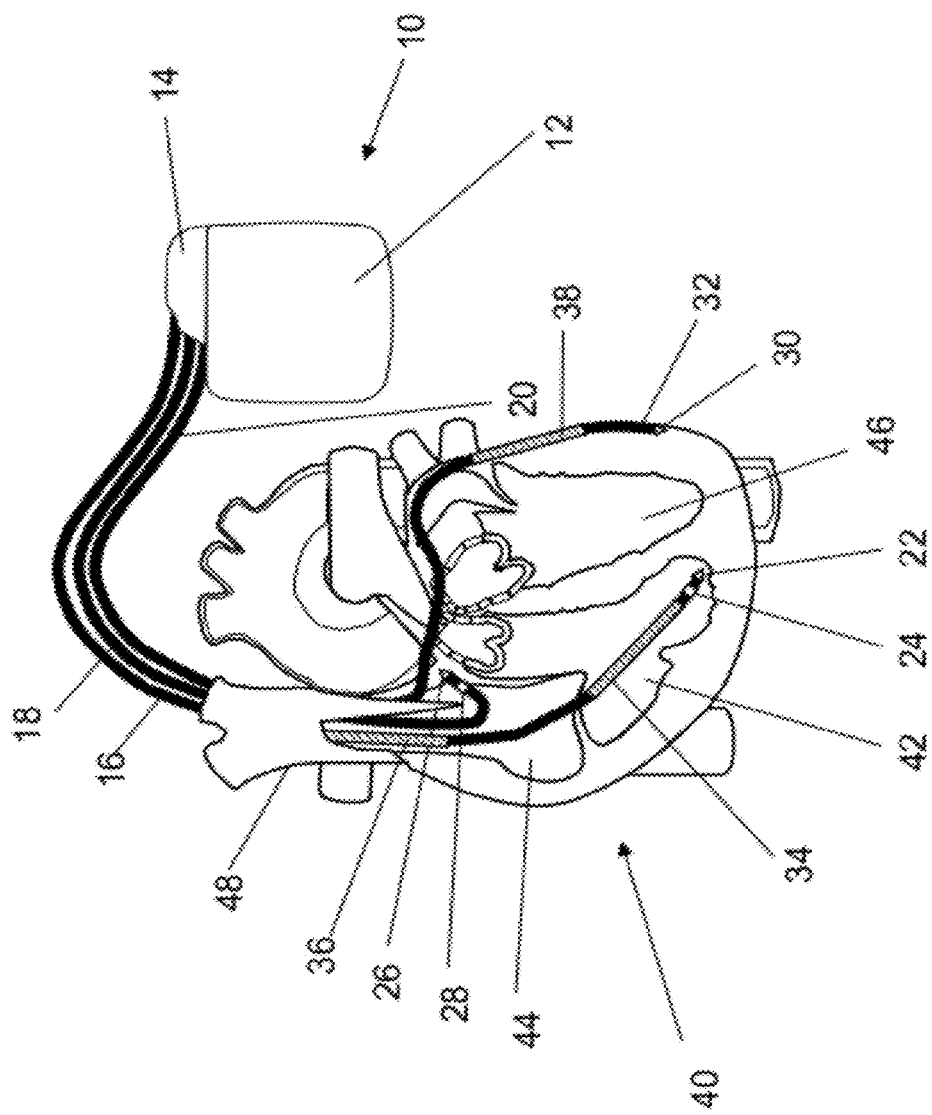
FIG. 1 shows a medical implant as a heart monitor.

FIG. 1 shows a heart monitor in the form of an implantable medical device, namely in the form of an implantable cardiac stimulator 10. The cardiac stimulator 10 is implemented as a biventricular cardiac pacemaker and cardioverter/defibrillator.

In a conventional arrangement, the cardiac stimulator 10 has a housing 12 made of metal, which can also be used as a large-area electrode. A so-called header 14 made of plastic is attached to the housing 12, which can bear sockets which receive corresponding plugs of electrode lines, in order to electrically connect electrodes on the electrode lines to electrical components in the interior of the housing 12.

In the exemplary cardiac stimulator 10 of FIG. 1, a total of three electrode lines are connected to the cardiac pacemaker 10, namely a right-ventricular electrode line 16, a right-atrial electrode line 18, and a left-ventricular electrode line 20. Each of these electrode lines 16, 18, and 20 carries a pair of comparatively small-area stimulation and sensing electrodes on its distal end, here a right-ventricular tip electrode RV-TIP 22 and a right-ventricular ring electrode RV-RING 24 on the distal end of the right-ventricular electrode line 16, a right-atrial tip electrode RA-TIP 26 and a right-atrial ring electrode RA-TIP 28 on distal end of the right-atrial electrode line 18, and a left-ventricular tip electrode LV-TIP 30 and a left-ventricular ring electrode LV-RING 32 on the distal end of the left-ventricular electrode line 20.

For the purpose of a defibrillation shock delivery, comparatively large-area defibrillation electrodes are additionally also provided, which are each implemented as a shock coil. Specifically, these include a right-ventricular shock electrode RV-COIL 34, which is positioned on the right-ventricular electrode line 16 close to its distal end. The right-ventricular electrode line 16 additionally carries a proximal shock electrode VC-COIL 36, which is provided for placement in the vena cava. A left-ventricular shock electrode LV-COIL 38 is situated close to the distal end of the left-ventricular electrode line 20.

FIG. 1 schematically shows how the individual electrodes are approximately positioned in the heart after implantation. Thus, FIG. 1 shows a schematic view of a heart 40 having its right ventricle 42, its right atrium 44, and its left ventricle 46. In addition, a section of the vena cava superior 48 is shown.

Figure 2:
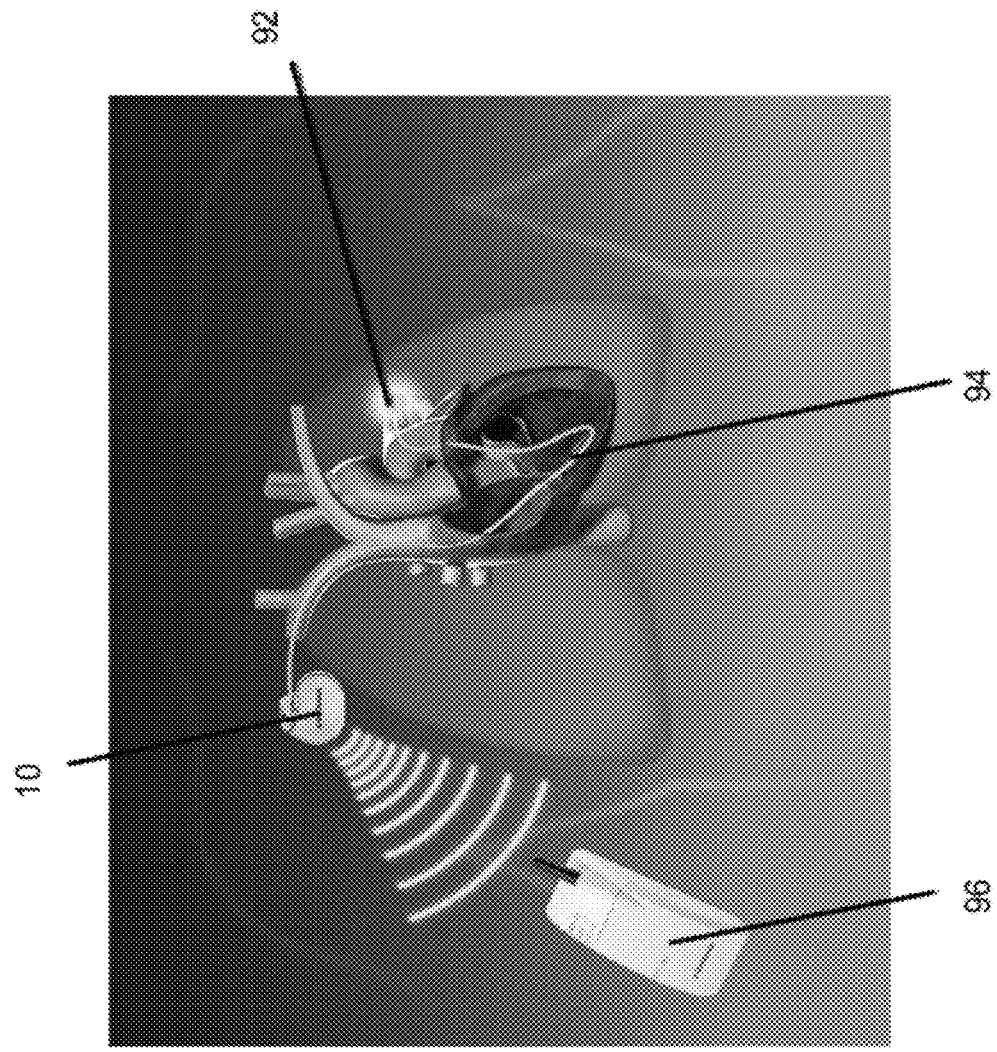
FIG. 2 shows a medical implant as a heart monitor together with an external device.

A pressure sensor 92 is shown in FIG. 2, which is connected via a cable 94 to the implantable medical device 10. The pressure sensor 92 can also contain a temperature sensor. The pressure sensor 92 and cable 94 are implemented so that the pressure sensor can be positioned in the pulmonary artery as shown in FIG. 2. The pressure sensor 92 is configured to deliver output signals corresponding to the hydrostatic pressure in the pulmonary artery, which varies periodically over time, in the form of pressure values.

Figure 3:
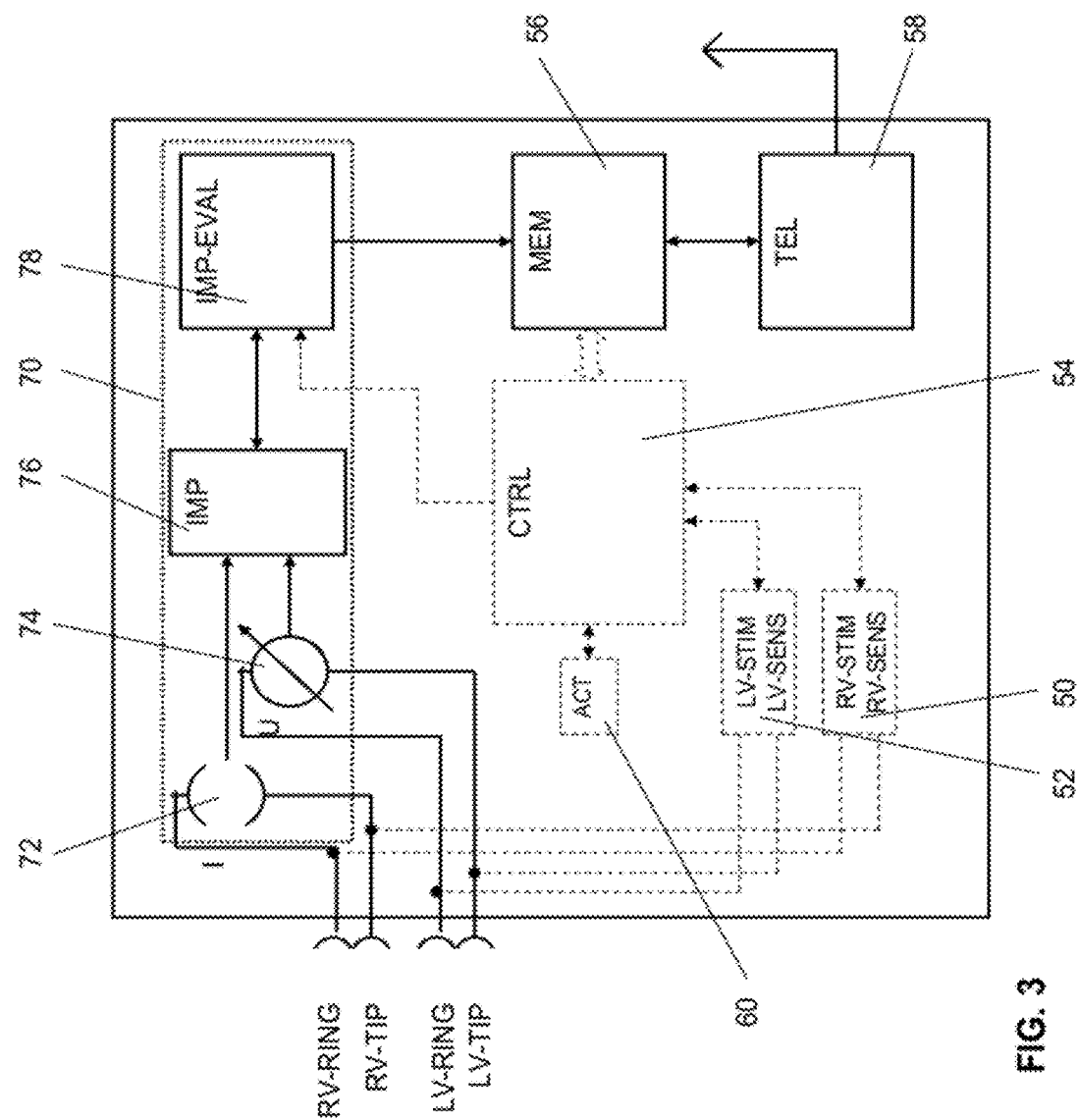
FIG. 3 shows a schematic block diagram of several components of the implant.
Figure 4:
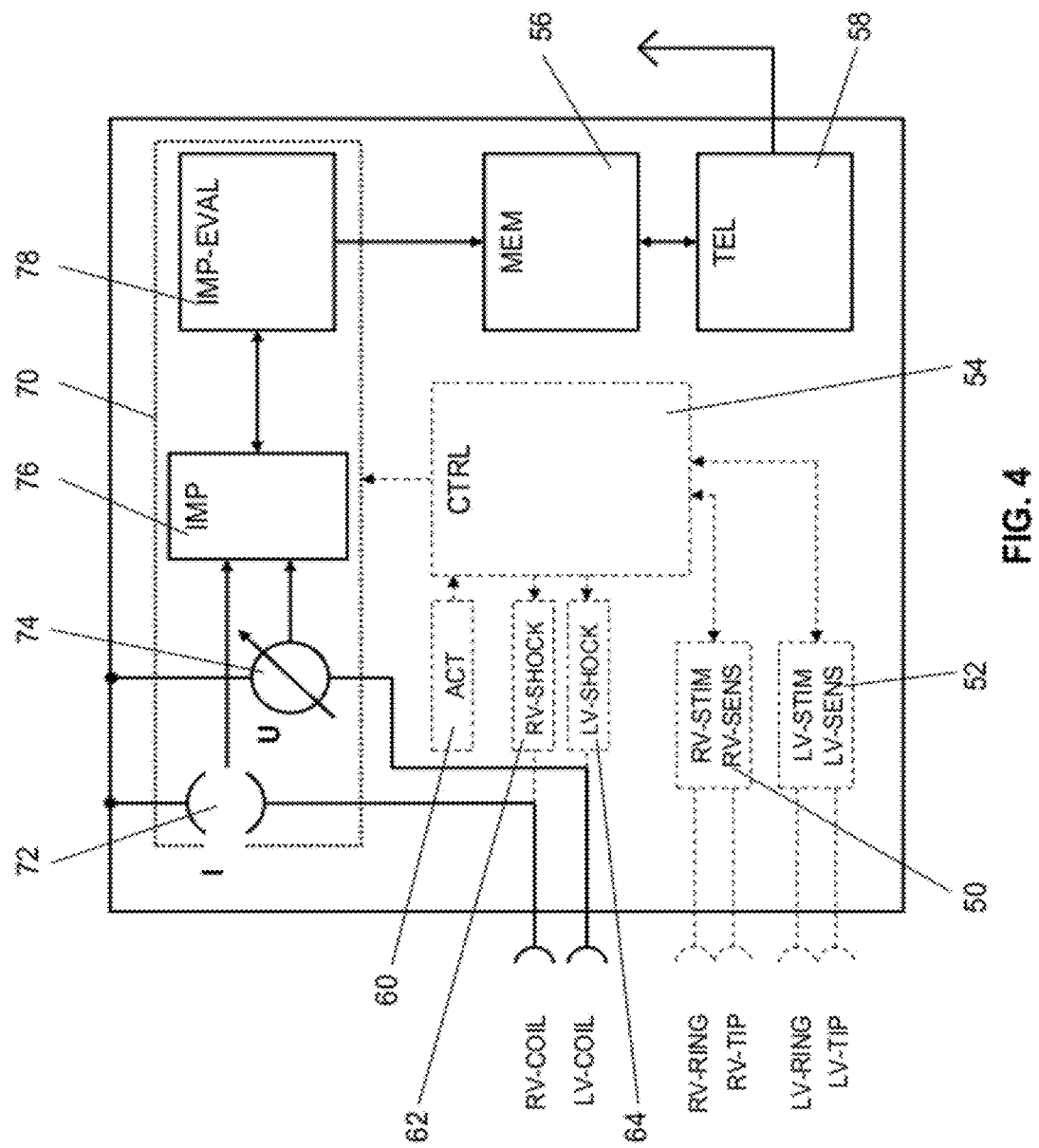
FIG. 4 shows a schematic block diagram of several components of an alternative version of the implant.

FIGS. 3 and 4 schematically illustrate some of the electronic components of the heart stimulator 10, which are positioned in its housing 12, namely a right-ventricular stimulation unit RV-STIM and a right-ventricular sensing unit RV-SENS, which are provided with a common reference numeral 50. The right-ventricular stimulation unit RV-STIM and the right-ventricular sensing unit RV-SENS are connected to the electrical terminal for the right-ventricular ring electrode RV-RING 24 and the right-ventricular tip electrode RV-TIP 26. Similarly, a left-ventricular stimulation unit LV-STIM and a left-ventricular sensing unit LV-SENS (shown with a common reference numeral 52) are connected to the electrical terminal for the left-ventricular tip electrode LV-TIP 30 and the left-ventricular ring electrode LV-RING 32. The stimulation and sensing units are additionally connected to a central control unit CTRL 54.

The control unit is additionally connected to an activity sensor 60, which can be a blood temperature sensor, a movement sensor, or a sensor for the oxygen saturation of the blood, and which accordingly delivers an output signal (an activity signal) which reflects the activity of a patient. The control unit CTRL 54 is connected to a memory MEM 56, which is in turn connected to a telemetry unit TEL 58. Using the telemetry unit TEL 58, data may be transmitted to and/or received from an external device 96 (see FIG. 2). The external device 96 can also be used as a relay station in order to transmit data from the implantable medical device (here the implantable medical cardiac stimulator 10) to a central service center.

The memory unit MEM 56 may be used for the purpose of buffering physiological or operating data acquired by the cardiac stimulator 10, if this data is to be transmitted via the telemetry unit TEL 58 to an external device. In addition, parameters or program data may also be stored in the memory unit MEM 56, which the control unit CTRL 54 accesses and which influence the operation of the cardiac stimulator 10.

FIG. 4 additionally also shows that for the case in which the cardiac stimulator 10 is a defibrillator, a right-ventricular shock generator RV-SHOCK 62 and a left-ventricular shock generator RV-SHOCK 64 may also be provided, which can each be connected to the control unit CTRL 54 and also to an electrical terminal RV-COIL for the right-ventricular shock electrode or a terminal LV-COIL for the left-ventricular shock electrode.

FIGS. 3 and 4 show a schematic view of an implant 10 or 10' having an impedance measuring unit 70, which has a power source 172, a voltage meter U 74, and an impedance determination unit IMP 76.

In the version of FIG. 3, the voltage meter U 74 is connected to a left-ventricular LV-TIP, which is positioned in a lateral vein branching from the coronary sinus, and a left-ventricular ring electrode LV-RING, which is also positioned in a lateral vein branching from the coronary sinus. The power supply unit 172 is connected to a right-ventricular tip electrode RV-TIP and to a right-ventricular ring electrode RV-RING (or more precisely to contacts for the terminals of these electrodes).

In the version of FIG. 4, the voltage measuring unit U 74 is connected to the left-ventricular defibrillation electrode LV-COIL and to the implant housing 12 as the second electrode. The power supply unit 172 is connected to the right-ventricular defibrillation electrode RV-COIL and also to the implant housing 12 as the second electrode.

For the impedance determination, the impedance determination unit IMP 76 is connected to both the power supply unit 172 and also to the voltage measuring unit U 74. The measured impedance value is relayed by the impedance determination unit IMP 76 to an evaluation unit IMP-EVAL 78. The evaluation unit IMP-EVAL 78 determines an end-diastolic impedance EDZ and an end-systolic impedance ESZ from the values collected by the impedance determination unit IMP 76 in the way described below.

In addition, the evaluation unit IMP-EVAL 78 derives a stroke impedance SZ from these values as the difference of end-systolic impedance ESZ and end-diastolic impedance EDZ (SZ=ESZ−EDZ). This is performed in connection with a plausibility check wherein a check is performed to see whether the end-diastolic impedance (EDZ) is less than the end-systolic impedance (ESZ).

Further values ascertained by the evaluation unit IMP-EVAL 78 are an ejection fraction (EF) for each cardiac cycle, which may be calculated from the stroke impedance SZ and the end-systolic impedance ESZ (EF~SZ/ESZ because EF=SV/EDV and SV~SY=SZ/(EDZ*ESZ) and EDV~1/EDZ), or from the end-diastolic conductivity (EDY) and the end-systolic conductivity (ESY), and also from a contractility variable which represents the contractility of the heart. All of these values are stored by the evaluation unit IMP-EVAL 78 in the memory MEM 76, preferably at regularly recurring saving times. A variable which determines these parameters or another variable determined from the intracardial (FIG. 3) or intrathoracic (FIG. 4) impedance may alternatively be used for evaluating the pressure signal as a measure for the stroke-by-stroke contractility or preload. In addition to the above-described electrode interconnections, other current and voltage paths are also conceivable for measuring the intracardial or intrathoracic impedance.

The evaluation unit IMP-EVAL 78 is also configured to calculate mean values for the stroke impedance, the EF variable, and/or the contractility for a respective period of time for each of various respiratory phases lying between two saving times, and to save these mean values in the memory MEM 56.

Furthermore, the evaluation unit IMP-EVAL 78 is also configured to establish trends for the variables ascertained by the evaluation unit IMP-EVAL 78 and to store corresponding trend values in the memory MEM 56.

The memory MEM 56 has an output connected to the telemetry unit TEL 58, which is configured to transmit the respective values stored in the memory 56 at regularly occurring transmission times from the telemetry unit 58 using a transmission unit. The values may then be received by an external device, and may be relayed to a service center, a physician, or the like, for example.

For the impedance measurement, the impedance measuring unit 70 injects a sub-threshold current between two electrodes of the electrode lines connected to the implant and/or the implant housing 12. The current preferably has the form of biphasic pulses having constant amplitude. The voltage drop (the voltage) caused by the current is measured via another electrode pair of the available electrodes. The measured voltage is proportional to the impedance of the tissue located in the measuring area. In an alternative version, the current-injecting electrodes and the electrodes for voltage measurement may be the same electrodes.

Figure 5:
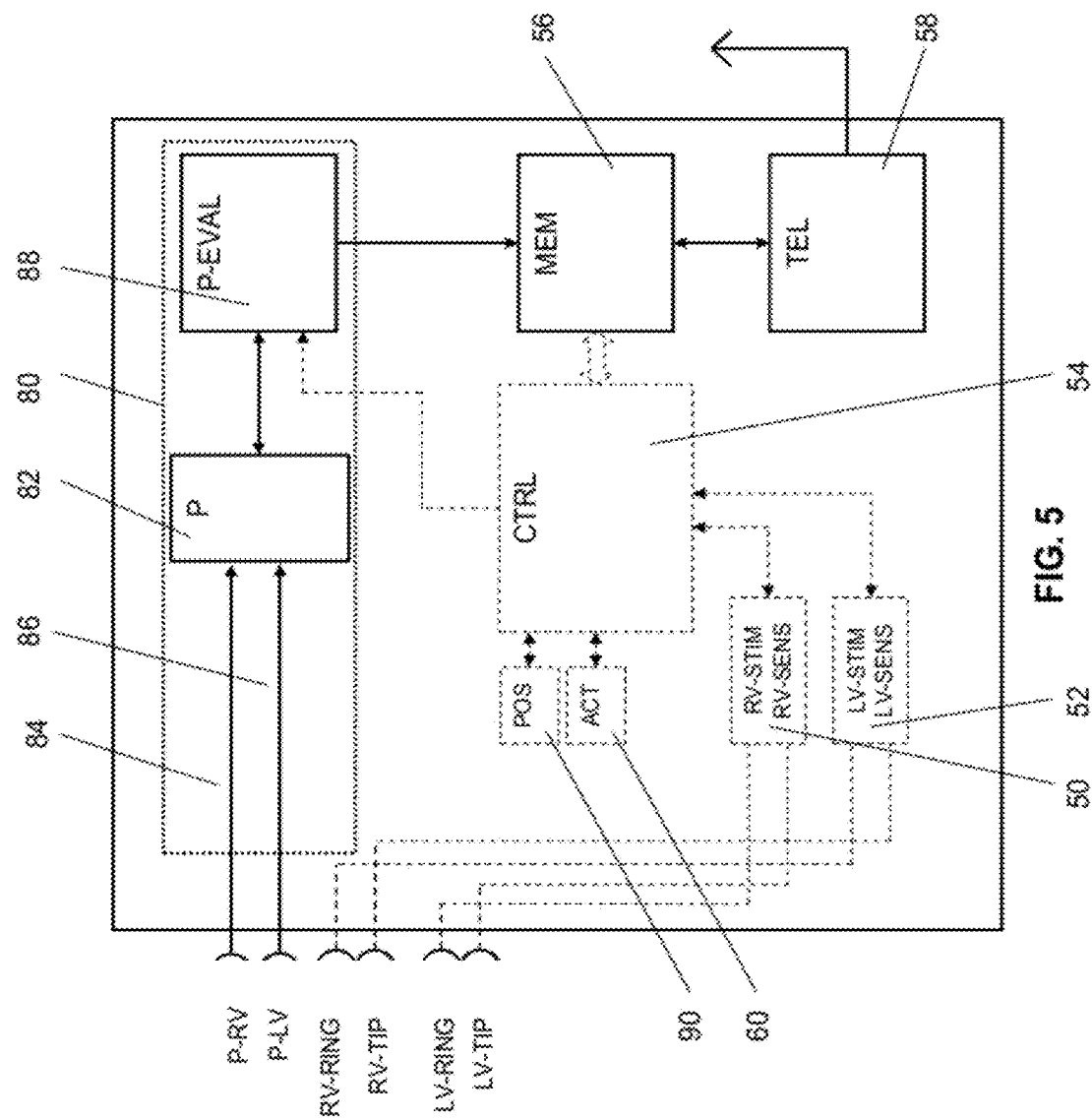
FIG. 5 shows a schematic block diagram of several components of a third version of the implant.

FIG. 5 shows a preferred version of the heart monitor wherein a blood pressure measuring unit 80 is provided instead of an impedance measuring unit. The blood pressure measuring unit 80 has a pressure acquisition unit 82 having an input connected via a line 84 to a terminal P-RV for a right-ventricular blood pressure sensor, and also via a line 86 to a terminal P-LV for a blood pressure sensor for acquiring the pressure in the left ventricle, or in the aorta, or in a peripheral artery. The right-ventricular blood pressure sensor P-RV is preferably positioned in the distal area of the right-ventricular electrode line 16 and delivers pressure values of the pulmonary circulation, while a left-ventricular pressure sensor P-LV delivers corresponding pressure values from the systemic circulation. The pressure values delivered by the pressure sensors P-RV and P-LV are processed by the pressure acquisition unit 82. An evaluation unit P-EVAL 88, which evaluates the processed pressure values as described below, is connected to the pressure acquisition unit 82.

The acquisition and evaluation of the pressure values is preferably executed as follows. Using the sensor system formed by the blood pressure measuring unit 80, a blood pressure is measured in the right ventricle and in the pulmonary artery. The patient's position may optionally be measured via a position sensor 90 in order to separately deal with recumbent and upright positions. The values thus acquired are evaluated by the evaluation unit 88 as follows:

1. the respiratory pressure curve is determined from characteristic points of the blood pressure signal, for example, from the maximum or the end-diastolic pressure of each cardiac cycle.
2. $(dP/dt)_{max}$ is determined for each cardiac cycle.
3. The points of each cycle (respiratory pressure; $(dP/dt)_{max}$) can be used to determine suitable parameters, such as minimum/maximum values, percentile;
   scattering dimensions; (A pathological change of the contractility could also be shown in amplified scattering at equal preload.)
   Slope parameters (e.g., mean slope, maximum slope, slope relative to a value derived from the graph) or parameters of suitable fit functions (possibly also a test of various fit functions, in order to recognize a pathologically caused change of the shape of the dependence of contractility (preload)).
   This parameter determination can be performed by graphing the points of each cycle (respiratory pressure, $(dP/dt)_{max}$) and analyzing the graph to derive the parameters. It should be understood that the graph need not be visually depicted, and rather can exist in the form of a collection of data which can be analyzed to derive the desired parameters (and which can preferably be visually depicted as well).

The parameters determined in step 3 can be compared to suitable reference values, such as earlier measurements or specified threshold values, which may be stored in the memory MEM 56. Further parameters, in particular trend parameters, may be derived from the time curve of the parameter or the difference from the reference value.

Display of the graph and/or the parameters can be performed in suitable external devices, for example, in an external device used for home monitoring, or in an independent device.

The evaluation unit or a separate analysis unit is preferably configured to perform a threshold value comparison in such a manner that various actions may be triggered upon exceeding/falling below a threshold value, such as sending an alarm signal to the attending physician, sending an alarm signal/instructions to the patient, e.g., requests to take medications or to find/contact a physician; modifying the control of a therapy device, e.g., adaptation of pacing parameters of a pacemaker/ICD, and/or of delivery of antitachycardial therapy (e.g., defibrillation shock); and/or administering a medication.

Instead of the respiratory curve of characteristic points of the blood pressure as a sensor variable A, other variables are also conceivable, such as intrathoracic impedance.

Similarly, instead of $(dP/dt)_{max}$ as sensor variable B, other variables such as intracardiac impedance and/or stroke volume are also conceivable as per the versions shown in FIGS. 2 and 3.

The heart monitor is configured in the exemplary version shown in FIG. 5 to perform blood pressure measurements both in the systemic and also in the pulmonary circulation, e.g., by blood pressure measurement in both ventricles. This also allows recognition of obstructive apnea, which is not well detectable solely by intrathoracic impedance measurement.

When the air tubes are closed during an apnea event, the lungs cannot stretch. For this reason, no reduction of the preload of the left ventricle occurs, as described above, and thus no variation is observed in $(dLVP/dt)_{max}$ and/or $(dAoP/dt)_{max}$. Here, LVP is the pressure in the left ventricle, or the starting value of a pressure sensor provided for placement in the left ventricle, and AoP is the pressure in the aorta or the starting value of a pressure sensor provided for placement in the aorta.

In contrast, the thoracic pressure is lowered entirely regularly, so that $(dRVP/dt)_{max}$ and/or $(dPAP/dt)_{max}$ have the typical variations. Here RVP is the pressure in the right ventricle or the starting value of a pressure sensor provided for placement in the right ventricle, and PAP is the pressure in the pulmonary artery or the starting value of a pressure sensor provided for placement in the aorta.

A reduction of the $(dP/dt)_{max}$-amplitude in the pulmonary circulation with uniform amplitude in the systemic circulation is therefore an indication of an event of obstructive sleep apnea. In a preferred version, the evaluation unit is configured to detect such a reduction of the $(dP/dt)_{max}$-amplitude with uniform amplitude in the systemic circulation, and to generate an apnea warning signal. A suitable therapy can be started, modified, or ended upon detection of the beginning or end of an apnea event. Further, apnea events may be monitored and data such as number, times of the occurrence, duration, strength of the measured effect, static parameters of this data, etc., can be displayed in a suitable way, for example, in an external device or via home monitoring.

The evaluation unit can also or alternatively be configured to differentiate between active and passive respiration.

During independent inhalation, the patient generates a partial vacuum in the thorax, by which air is sucked into the lungs. In contrast, during artificial respiration, air is pressed into the lungs by an overpressure. It therefore follows that active and passive respiration have the same curve of the lung volume, but the thoracic pressures are in counter phase. As described above, the lung volume acts on the left-ventricular contractility via the Frank-Starling mechanism, while the thoracic pressure is reflected in an amplitude variation of the characteristic points of each cardiac cycle (particularly clearly in the pulmonary circulation). The phase relationship between $(dLVP/dt)_{max}$ and/or $(dAoP/dt)_{max}$ and $P_{thoracic}$ (e.g., from PAP) thus gives an indication of whether the patient is breathing independently or is ventilated. The evaluation unit therefore preferably allows determination of the phase relationship between $(dLVP/dt)_{max}$ and/or $(dAoP/dt)_{max}$ and $P_{thoracic}$.

The heart monitor of the invention allows the Frank-Starling mechanism to be acquired, i.e., the dependence of the contractility on the preload. This allows a significantly more detailed image of the output capability of the examined ventricle than the one provided by merely averaging all $(dP/dt)_{max}$ values.

The variation of the preload occurs spontaneously, i.e., it does not have to be specified externally, for example, by a measuring protocol.

As noted, instead of a pressure-based implementation of the heart monitor, an impedance-based implementation is also conceivable, which can use sensor systems already present in pacemaker/ICDs.

The data evaluation can also be performed in an evaluation unit of an external device, such as a patient device 96 (see FIG. 2) or a central service center, instead of by an evaluation unit of an implantable medical device. For this purpose, corresponding blood pressure values or impedance values may be transmitted using a telemetry unit to the external device.

Figures 6A, 6B:
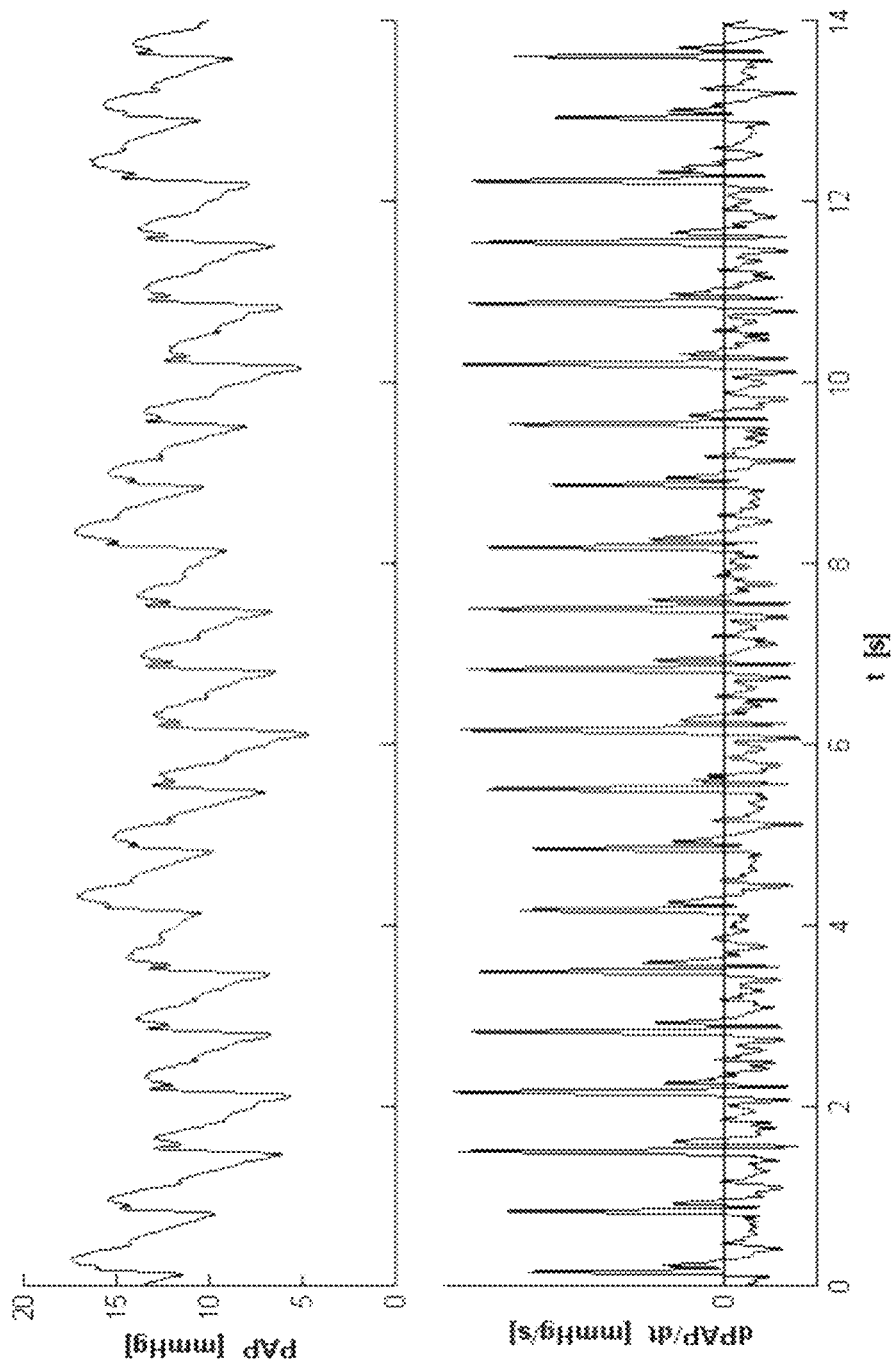
FIGS. 6A and 6B: show the dependence of blood pressure and the first derivative of the blood pressure on the respiration.

FIG. 6A illustrates the blood pressure in the pulmonary artery as obtained in animal experiments on sheep under ventilation. The blood pressure is shown over 14 seconds and over 3 respiration cycles, and over 21 cardiac actions. The respiration-related variations in the thoracic pressure are shown in oscillations of the end-diastolic pressure (minimum of each cardiac cycle) and in the maximum pressure.

The derivative of the blood pressure according to time is shown in FIG. 6B. The peaks upward correspond to $(dP/dt)_{max}$ in each cardiac cycle. The amplitudes oscillate with approximately 180° phase shift to the thoracic pressure.

Preferred versions of the invention have been described above for purposes of illustration, and numerous modifications and variations to these versions are possible. The invention is not intended to be limited to the preferred versions, but rather is intended to be limited only by the claims set out below. Thus, the invention encompasses all different versions that fall literally or equivalently within the scope of these claims.

What is claimed is:
1. An implantable cardiac stimulator including:
   a. a preload determination unit configured to quantify the preloads of the right and left ventricles of a heart over several cardiac cycles,
   b. a contractility determination unit configured to quantify the contractilities of the right and left ventricles over the cardiac cycles,
   c. an evaluation unit configured to determine when the right ventricle's contractility decreases at the same time the left ventricle's contractility remains uniform, wherein the implantable cardiac stimulator is further configured to modify therapy delivered to the heart in dependence on the evaluation unit's determination.

2. An implantable cardiac stimulator of claim 1 wherein:
   a. the preload determination unit is configured to determine one or more of:
      (1) blood pressure;
      (2) intrathoracic impedance;
      (3) intracardiac impedance; and
      (4) stroke volume,
      for each ventricle;
   b. the contractility determination unit is configured to determine one or more of:
      (1) blood pressure;
      (2) intracardiac impedance; and
      (3) stroke volume,
      for each ventricle.

3. The implantable cardiac stimulator of claim 1 further including a sensor configured to determine at least one of patient activity and patient position, wherein the evaluation unit is configured to provide a representation of the dependence of contractility with respect to:
   a. the preload, and
   b. at least one of patient activity and patient position,
   for each of the ventricles.

4. An implantable cardiac stimulator including:
   a. a preload determination unit configured to:
      (1) determine the preload of each of the right and left ventricles for a cardiac cycle, and
      (2) provide preload values representing the determined preloads,
   b. a contractility determination unit configured to:
      (1) determine the contractility of each of the right and left ventricles for the cardiac cycle, and
      (2) provide contractility values representing the determined contractilities,
   c. an evaluation unit configured to:
      (1) receive the preload values and the contractility values for each cardiac cycle in a series of cardiac cycles, and
      (2) determine:
         (a) relationships between the contractility values and the preload values for each of the ventricles over the series of cardiac cycles,
         (b) the presence of:
            i. decreasing contractility of the right ventricle, while
            ii. the contractility of the left ventricle is uniform,
            over the series of cardiac cycles, such presence being indicative of apnea,
   wherein the implantable cardiac stimulator is further configured to:
   A. transmit an alarm signal from the cardiac stimulator, and/or
   B. modify stimulation delivered to the heart,
   in dependence on the evaluation unit's determination.

5. The implantable cardiac stimulator of claim 4 further including:
   a. a stimulator housing wherein the preload determination unit and the contractility determination unit are situated;
   b. a first electrode line leading from the housing, the first electrode line having a first electrode thereon;
   c. a second electrode line leading from the housing, the second electrode line having a second electrode thereon;
   d. an impedance determination unit:
      (1) configured to determine an impedance between at least two of the first electrode, the second electrode, and the housing;
      (2) wherein the impedance determination unit is provided as a component of at least one of the preload determination unit and the contractility determination unit.

6. The implantable cardiac stimulator of claim 4 wherein the contractility determination unit includes a blood pressure sensor.

7. The implantable cardiac stimulator of claim 4 wherein the contractility determination unit is configured to provide the contractility values in dependence on pressure values representing ventricular pressures.

8. The implantable cardiac stimulator of claim 4 wherein the contractility determination unit is configured to determine at least one of:
   a. intracardiac impedance, and
   b. stroke volume.

9. The implantable cardiac stimulator of claim 4 wherein the preload determination unit includes a blood pressure sensor.

10. The implantable cardiac stimulator of claim 4 wherein the preload determination unit is configured to determine at least one of:
    a. intracardiac impedance, and
    b. stroke volume.

11. The implantable cardiac stimulator of claim 4 wherein the preload determination unit is configured to determine at least one of:
    a. pressure values representative of thoracic pressure, and
    b. a thoracic pressure differential.

12. The implantable cardiac stimulator of claim 4:
    a. further including an activity sensor configured to detect patient activity, and
    b. the evaluation unit further determines a relationship between the contractility values, the preload values, and patient activity over the series of cardiac cycles.

13. The implantable cardiac stimulator of claim 4:
    a. further including a position sensor configured to detect patient position, and
    b. the evaluation unit further determines a relationship between the contractility values, the preload values, and patient position over the series of cardiac cycles.

14. The implantable cardiac stimulator of claim 4 further including:
    a. a stimulator housing wherein the preload determination unit and the contractility determination unit are situated;
    b. a first electrode line leading from the housing, the first electrode line having a first electrode thereon;
    c. a second electrode line leading from the housing, the second electrode line having a second electrode thereon;
    d. a blood pressure sensor:
       (1) configured to determine hydrostatic blood pressure;
       (2) wherein the blood pressure sensor is provided as a component of one of the preload determination unit and the contractility determination unit.

15. The implantable cardiac stimulator of claim 4 wherein the evaluation unit is further configured to:
    a. obtain a measure of pressure from a pressure sensor in a pulmonary vessel, and
    b. generate an apnea warning signal in dependence on:
       (1) the contractility values for the ventricles over the series of cardiac cycles, and
       (2) the measure of pressure in the pulmonary vessel.

16. The implantable cardiac stimulator of claim 4 further including a sensor configured to determine at least one of patient activity and patient position, wherein the evaluation unit is configured to determine the relationship between the contractility values and the preload values for each of the right and left ventricles at one or more:
  a. patient activity levels, and/or
  b. patient positions.

17. An implantable cardiac stimulator including:
  a. a first pressure sensor configured to detect the pressure in the right ventricle of a heart,
  b. a second pressure sensor configured to detect the pressure in the left ventricle of a heart,
  c. a preload determination unit configured to determine the preload of each of the right and left ventricles for a cardiac cycle, wherein:
    (1) the right ventricle's determined preload is dependent on the maximum pressure detected by the first pressure sensor over the cardiac cycle,
    (2) the left ventricle's determined preload is dependent on the maximum pressure detected by the second pressure sensor over the cardiac cycle,
  d. a contractility determination unit configured to determine the contractility of each of the right and left ventricles for a cardiac cycle, wherein:
    (1) the right ventricle's determined contractility is dependent on the maximum of the derivative of the pressure detected by the first pressure sensor over the cardiac cycle,
    (2) the left ventricle's determined contractility is dependent on the maximum of the derivative of the pressure detected by the second pressure sensor over the cardiac cycle,
  e. an evaluation unit configured to:
    (1) provide a representation of dependence of contractility with respect to the preload for each ventricle over several cardiac cycles, thereby providing an indication of the Frank-Starling mechanism for each ventricle,
    (2) generate an apnea warning signal when the right ventricle's determined contractility decreases while the left ventricle's determined contractility remains uniform,
  wherein the implantable cardiac stimulator delivers therapy to the heart in dependence on the apnea warning signal.

* * * * *